(12) United States Patent
Lee et al.

(10) Patent No.: US 8,724,105 B2
(45) Date of Patent: May 13, 2014

(54) NANO PARTICLE TRACKING DEVICE, CHANNEL STRUCTURE OF THE NANO PARTICLE TRACKING DEVICE, AND METHOD OF FABRICATING THE CHANNEL STRUCTURE OF THE NANO PARTICLE TRACKING DEVICE

(75) Inventors: June-young Lee, Anyang-si (KR); Hee-jeong Jeong, Seoul (KR); Seong-ho Cho, Gwacheon-si (KR); Su-hyeon Kim, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 422 days.

(21) Appl. No.: 13/160,854

(22) Filed: Jun. 15, 2011

(65) Prior Publication Data

US 2012/0194811 A1 Aug. 2, 2012

(30) Foreign Application Priority Data

Jan. 27, 2011 (KR) ........................ 10-2011-0008252

(51) Int. Cl.
*G01N 1/10* (2006.01)
*B82Y 15/00* (2011.01)
*B01L 3/00* (2006.01)

(52) U.S. Cl.
CPC . *B82Y 15/00* (2013.01); *G01N 1/10* (2013.01); *B01L 3/502707* (2013.01); *Y10S 977/953* (2013.01); *Y10S 977/957* (2013.01); *Y10S 977/958* (2013.01)
USPC ........ 356/246; 435/287.1; 422/503; 977/953; 977/957; 977/958

(58) Field of Classification Search
None
See application file for complete search history.

(56) References Cited

U.S. PATENT DOCUMENTS

| 5,637,469 | A * | 6/1997 | Wilding et al. ............ 435/287.1 |
| 8,184,284 | B2 * | 5/2012 | Ebstein ........................ 356/301 |
| 8,202,492 | B2 * | 6/2012 | Linder et al. .................. 422/503 |
| 2004/0035701 | A1 | 2/2004 | Han et al. |
| 2006/0183112 | A1 * | 8/2006 | Min et al. ........................ 435/5 |
| 2007/0054391 | A1 * | 3/2007 | Lee et al. ................... 435/287.2 |
| 2008/0316490 | A1 * | 12/2008 | Yen et al. ....................... 356/445 |
| 2011/0215002 | A1 * | 9/2011 | Martinez ...................... 977/958 |
| 2011/0262307 | A1 * | 10/2011 | Packirisamy et al. ....... 422/82.08 |

FOREIGN PATENT DOCUMENTS

| JP | 2002139499 A | 5/2002 |
| JP | 2005195492 | 7/2005 |
| JP | 2006337245 | 12/2006 |
| KR | 1020100077810 A | 7/2010 |

* cited by examiner

*Primary Examiner* — Gregory J Toatley
*Assistant Examiner* — Juan D Valentin, II
(74) *Attorney, Agent, or Firm* — Leydig, Voit & Mayer, Ltd.

(57) ABSTRACT

A nano particle tracking device includes a channel structure. The channel structure of the nano particle tracking device includes a pair of microchannels in which a specimen including nano particles is accommodated and which face each other, at least one nano channel which is between the pair of microchannels, which connects the pair of microchannels to each other and through which the nano particles in the specimen are moved, and a nano grating below the nano channel and crossing the nano channel perpendicularly.

27 Claims, 12 Drawing Sheets

NANO PARTICLE TRACKING DEVICE, CHANNEL STRUCTURE OF THE NANO PARTICLE TRACKING DEVICE, AND METHOD OF FABRICATING THE CHANNEL STRUCTURE OF THE NANO PARTICLE TRACKING DEVICE

CROSS-REFERENCE TO RELATED APPLICATIONS

This application claims priority to Korean Patent Application No. 10-2011-0008252, filed on Jan. 27, 2011, and all the benefits accruing therefrom under 35 U.S.C. §119, the disclosure of which is incorporated herein in its entirety by reference.

BACKGROUND

1. Field

Provided are nano particle tracking devices, channel structures of the nano particle tracking devices, and methods of fabricating the channel structures of the nano particle tracking devices, and more particularly, nano particle tracking devices having channel structures in which position change and movement speed of nano particles, such as deoxyribonucleic acid ("DNA"), biomolecules, chemical molecules, or the like, are measured, the channel structures of the nano particle tracking devices, and methods of fabricating the channel structures of the nano particle tracking devices.

2. Description of the Related Art

As bio-related technologies are developed, analysis and diagnosis of genes, analysis of base sequences, and the like are becoming more significant, and demand therefore is gradually increasing. As such, various analysis or measurement systems for carrying out a large amount of tests by using a small sample within a short time have been developed. In addition, in order to implement such systems, for example, fine fluid elements, such as a lab on a chip and the like, have been spotlighted.

Nano particle tracking devices measure activity of single molecules or the like by limiting the number of nano-scale biomolecules, chemical molecules, or the like within a small space having a width of several tens or hundreds of nanometers (nm). Such nano particle tracking devices may be used in a nucleic acids sequence analysis device, a nano fluidic device, a particle image velocimetry, a single-molecule detection device, a gene mapping device, or the like, for example.

Generally, nano particle tracking devices measure position change or movement speed of nano particles by using a microscope and a photodetection device, such as a charged coupled device ("CCD"), while moving the nano particles by using an electrophoresis method, for example, within an array of nano channels having a width of several tens or hundreds of nm. For example, after images showing movement of nano particles are captured by using a CCD and a microscope, movement speed of the nano particles can be measured by analyzing image data. However, when all of the images showing movement of the nano particles are accumulated, the amount of image data to be processed is great. In addition, due to limitations in response speed and signal processing speed of photodetection devices, measurement errors may occur.

SUMMARY

Provided are nano particle tracking devices that measure position change and movement speed of nano particles quickly and precisely.

Also provided are channel structures of nano particle tracking devices.

Also provided are methods of fabricating the nano particle tracking devices.

Additional aspects will be set forth in part in the description which follows and, in part, will be apparent from the description, or may be learned by practice of the presented embodiments.

According to an aspect of the present invention, a channel structure includes a pair of microchannels in which a specimen including nano particles is accommodated and which face each other, at least one nano channel which is between the pair of microchannels, which connects the pair of microchannels to each other and through which nano particles in the specimen are moved between the pair or microchannels, and a nano grating below the nano channel and crossing the nano channel perpendicularly.

The nano grating may include a pattern of a plurality of parallel opaque bars which are arranged at regular intervals.

A thickness of the nano grating may be greater than a skin depth of a material of the nano grating.

A distance between adjacent parallel opaque bars may be less than a wavelength of visible light.

The channel structure may further include a first transparent substrate, a channel forming layer on the first transparent substrate, and a second transparent substrate on the channel forming layer.

The pair of microchannels may extend through the channel forming layer and the first transparent substrate, the nano channels may be on an upper surface of the channel forming layer between the pair of microchannels, and the nano grating may be on a top surface of the first transparent substrate between the pair of microchannels and may be covered by the channel forming layer.

The channel structure may further include via holes through which the specimen is provided to the pair of microchannels, and connected to at least one of two end portions of each of the pair of microchannels.

The via holes may extend through at least the first transparent substrate or at least the second transparent substrate.

The channel structure may further include a first transparent substrate, a channel forming layer on the first transparent substrate, a junction layer on the channel forming layer; and a second transparent substrate on the junction layer.

The pair of microchannels may extend through the junction layer, the channel forming layer, and the first transparent substrate, the nano channel may be on an upper surface of the channel forming layer between the pair of microchannels, and the nano grating may be on the top surface of the first transparent substrate between the pair of microchannels and may be covered by the channel forming layer.

The via holes may extend through the second transparent substrate and the junction layer, or through at least the first transparent substrate.

The junction layer may include polysilicon.

The junction layer may include an oxide layer which is an oxidized surface of the polysilicon.

According to another aspect of the present invention, a nano particle tracking device includes the channel structure having the above-described structure, and a photodetector below the channel structure in a region corresponding to the nano channel.

The nano particle tracking device may further include a band pass filter between the channel structure and the photodetector.

The channel structure may include a plurality of nano channels, and the nano particle tracking device may further include one photodetector for each of the nano channels.

According to another aspect of the present invention, a method of fabricating a channel structure includes forming a nano grating having a pattern of a plurality of parallel opaque bars arranged at regular intervals on a top surface of a first transparent substrate, forming a channel forming layer on the first transparent substrate and covering the nano grating, forming a junction layer on the channel forming layer, forming nano channels in a direction perpendicular the nano grating by patterning portions of the junction layer corresponding to the nano grating, forming a pair of microchannels which is connected to end portions of each of the nano channels by partially etching the junction layer, the channel forming layer, and the first transparent substrate, and bonding a second transparent substrate onto the junction layer.

The method may further include, after the channel forming layer is formed, planarizing a top surface of the channel forming layer.

The junction layer may include polysilicon. The method may further include, before the second transparent substrate is bonded onto the junction layer, forming an oxide layer covering the junction layer by oxidizing a surface of the junction layer.

The method may further include forming via holes through the second transparent substrate and the junction layer, which are connected to an end portion of each of the microchannels.

The method may further include forming via holes at least through the first transparent substrate, which are connected to an end portion of each of the microchannels.

According to another aspect of the present invention, a method of fabricating a channel structure includes forming a nano grating having a pattern of a plurality of parallel opaque bars arranged at regular intervals on a top surface of a first transparent substrate, forming a channel forming layer on the first transparent substrate and covering the nano grating, forming nano channels in a direction perpendicular to the nano grating by patterning portions of a top surface of the channel forming layer corresponding to the nano grating, forming a pair of microchannels which is connected to end portions of each of the nano channels by partially etching the channel forming layer and the first transparent substrate, and bonding a second transparent substrate onto the channel forming layer.

The method may further include forming via holes through at least the first transparent substrate or at least the second transparent substrate, which are connected to an end portion of each of the microchannels.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
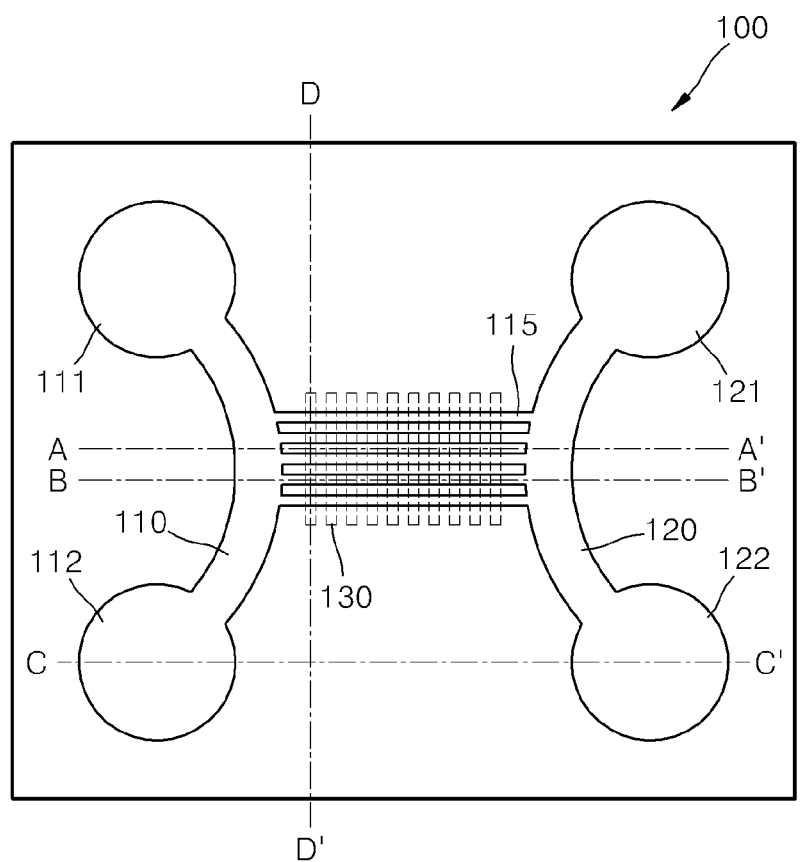
FIG. 1 schematically illustrates an embodiment of a channel structure of a nano particle tracking device, according to the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, "connected" includes physically and/or fluidly connected. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "below," "lower," "above," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "lower" relative to other elements or features would then be oriented "above" or "upper" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

FIG. 1 schematically illustrates an embodiment of a channel structure 100 of a nano particle tracking device, according to the present invention. Referring to FIG. 1, the channel structure 100 according to the present embodiment may include a pair of microchannels 110 and 120 in which a specimen is accommodated, nano channels 115 that are physically and fluidly connected between the pair of microchannels 110 and 120 and through which nano particles in the specimen are moved, and a nano grating 130 disposed below the nano channels 115 to cross the nano channels 115 perpendicularly. As illustrated in FIG. 1, a side surface of the microchannel 110 and a side surface of the microchannel 120 may face each other. In FIG. 1, the microchannels 110 and 120 are curved in a plan view so that a distance between central portions of the microchannels 110 and 120 is shorter than a distance between end portions of the microchannels 110 and 120. However, the present invention is not limited thereto and the microchannels 110 and 120 may be straight line-shaped and parallel to each other in the plan view. Via holes 111, 112, 121, and 122 through which the specimen is provided may be further on the end portions of the microchannels 110 and 120. Although four via holes 111, 112, 121, and 122 are illustrated in FIG. 1, the present invention is not limited thereto. In one embodiment, for example, only one via hole may be connected to each of the microchannels 110 and 120.

The nano channels 115 may be connected between the facing side surfaces of the microchannels 110 and 120. In FIG. 1, five nano channels 115 are illustrated. However, there is no limitation in the number of nano channels 115. In one embodiment, for example, if necessary, only one nano channel 115 may be between the micochannels 110 and 120, or six or more nano channels 115 may be therebetween. The nano channels 115 may have a width and a height that allow fine nano particles, such as biomolecules, chemical molecules, or the like, in the specimen to pass single-file therethrough. In one embodiment, for example, the width and the height of each nano channel 115 may be several tens or hundreds of nanometers (nm). In this regard, for example, when nano particles in the specimen accommodated in the first microchannel 110 are moved to the second microchannel 120, the nano particles may be moved single-file through each of the nano channels 115. Dimensions of the nano channels 115 may be relative smaller than dimensions of the microchannels 110 and 120.

The nano grating 130 is arranged below the nano channels 115. In the present embodiment, for example, as illustrated in FIG. 1, the nano grating 130 may have a pattern of a plurality of bars arranged at regular intervals and parallel to each other, and which cross the nano channels 115 perpendicularly. The nano grating 130 may include an opaque material. Thus, the nano grating 130 may include a plurality of bars that do not transmit light, and a plurality of slits that are defined between the bars and that transmit light. In this regard, while the nano particles are moved through the nano channels 115, the nano particles are repeatedly positioned over the opaque bars of the nano grating 130 or may be positioned over the slits of the nano grating 130. Thus, when viewed from below the nano grating 130, the nano particles may be repeatedly hidden by the nano grating 130 at regular intervals. By using this phenomenon, as the nano particles are moved through the nano channels 115, position and speed of the nano particles may be measured. The measuring method will be described in more detail later.

Figure 2:
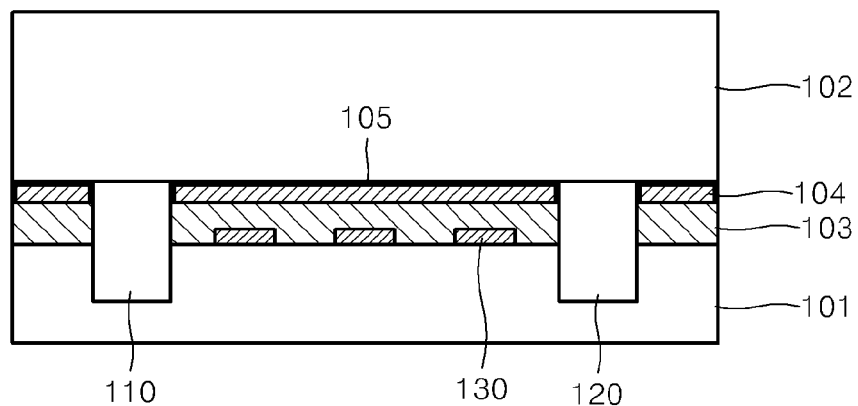
FIG. 2 is a cross-sectional view of the channel structure of FIG. 1, taken along line A-A' of FIG. 1.
Figure 3:
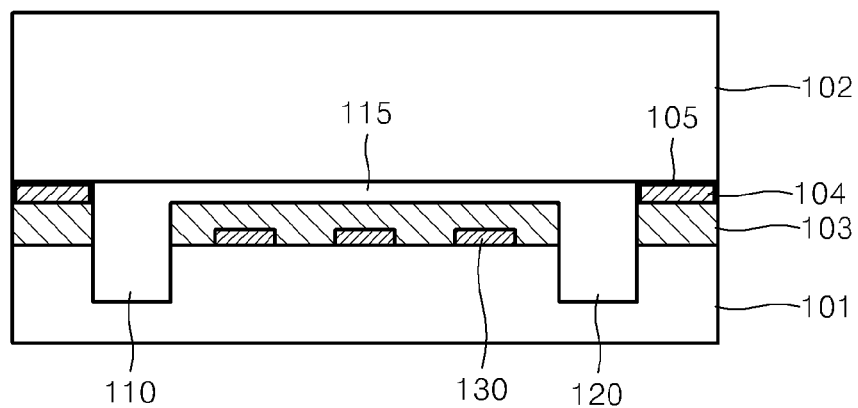
FIG. 3 is a cross-sectional view of the channel structure of FIG. 1, taken along line B-B' of FIG. 1.
Figure 4:
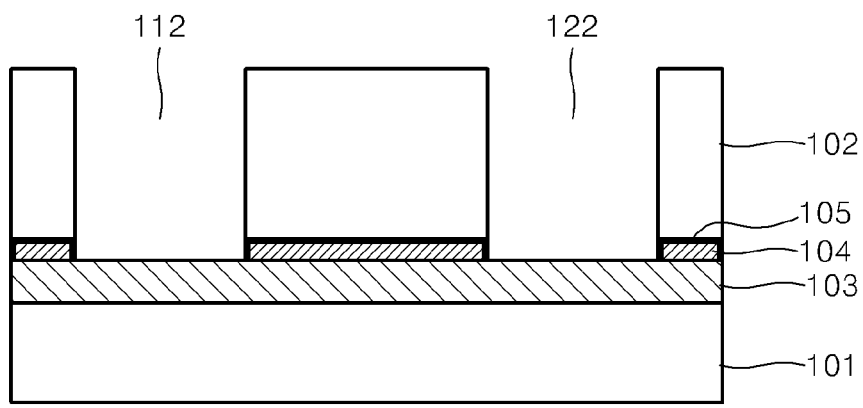
FIG. 4 is a cross-sectional view of the channel structure of FIG. 1, taken along line C-C' of FIG. 1.
Figure 5:
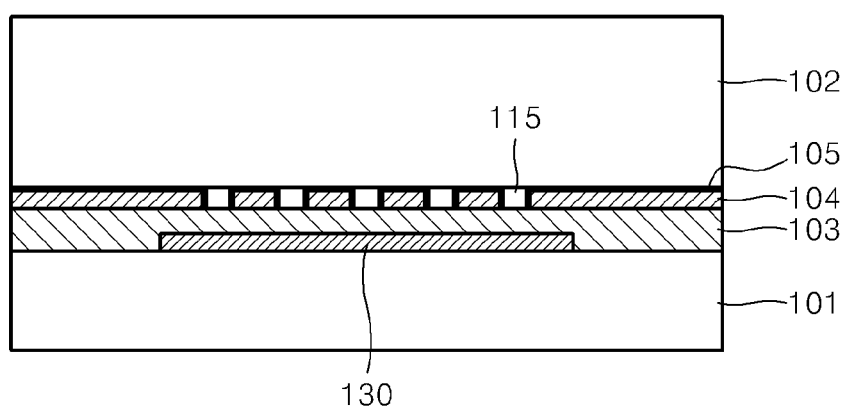
FIG. 5 is a cross-sectional view of the channel structure of FIG. 1, taken along line D-D' of FIG. 1.

The above-described microchannels 110 and 120, the nano channels 115, and the nano grating 130 may be on a transparent substrate. FIGS. 2 through 5 are cross-sectional views schematically illustrating the channel structure 100 including the microchannels 110 and 120, the nano channels 115, and the nano grating 130 on a transparent substrate. In the illustrated embodiment, for example, FIG. 2 is a cross-sectional view of the channel structure 100 taken along line A-A' of FIG. 1, FIG. 3 is a cross-sectional view of the channel structure 100 taken along line B-B' of FIG. 1, FIG. 4 is a cross-sectional view of the channel structure 100 taken along line C-C' of FIG. 1, and FIG. 5 is a cross-sectional view of the channel structure 100 taken along line D-D' of FIG. 1.

First, FIG. 2 is a cross-sectional view of the channel structure 100 taken along a barrier rib between two adjacent nano channels 115 along line A-A'. Referring to FIG. 2, the channel structure 100 may include a first transparent substrate 101, a channel forming layer 103 disposed on the first transparent substrate 101, a junction layer 104 disposed on the channel forming layer 103, and a second transparent substrate 102 disposed on the junction layer 104. The first and second transparent substrates 101 and 102 may include glass or polydimethylsiloxane ("PDMS"), for example. In addition, the channel forming layer 103 may include a transparent oxide, such as $SiO_2$. The junction layer 104 is conducive to bonding the second transparent substrate 102 to the channel forming layer 103 and may include polysilicon, for example.

As illustrated in FIG. 2, the microchannels 110 and 120 may extend through a top surface of the first transparent substrate 101, and through portions of the channel forming layer 103 and the junction layer 104 corresponding to the microchannels 110 and 120. The nano grating 130 is on the top surface of the first transparent substrate 101 between the two microchannels 110 and 120 and is covered (e.g., overlapped) by the channel forming layer 103. In addition, the junction layer 104 may be covered by an oxide layer 105 which electrically insulates the junction layer 104. The oxide layer 105 may be formed by oxidizing a surface of the junction layer 104. In regard to this, portions of the junction layer 104 between the nano channels 115 may act as barrier ribs between the nano channels 115.

FIG. 3 is a cross-sectional view of the channel structure 100 taken along one nano channel 115 along line B-B'. Compared to FIG. 2, in FIG. 3, portions of the junction layer 104 corresponding to the nano channels 115 are absent, thereby forming the nano channels 115. Thus, the two microchannels 110 and 120 may be connected to each other via the nano channels 115. Thus, the nano particles in the specimen accommodated in the microchannels 110 and 120 may be moved to the microchannels 120 and 110, respectively, through the nano channels 115. Portions of a top surface of the channel forming layer 103 between the microchannels 110 and 120 are bottom surfaces of the nano channels 115. As described above, the nano grating 130 may be arranged on the first transparent substrate 101 below the nano channels 115 to cross the nano channels 115.

FIG. 4 is a cross-sectional view of the channel structure 100 taken along the via holes 112 and 122 on ends of the microchannels 110 and 120 along line C-C'. Referring to FIG. 4, the via holes 112 and 122 extend through an entire thickness of the second transparent substrate 102. The via holes 112 and 122 may be respectively physically and fluidly connected to the microchannels 110 and 120, and the specimen may be provided to the microchannels 110 and 120 through the via holes 112 and 122. To this end, portions of the junction layer 104 corresponding to the via holes 112 and 122 may be penetrated. Thus, bottom surfaces of the via holes 112 and 122 may be portions of the top surface of the channel forming layer 103. According to an alternative embodiment, the via holes 112 and 122 may extend through an entire thickness of the channel forming layer 103, and thus the bottom surfaces of the via holes 112 and 122 may be portions of the top surface of the first transparent substrate 101. In one embodiment, for example, the via holes 112 and 122 and the microchannels 110 and 120 illustrated in FIG. 3 may have a common bottom surface.

In addition, FIG. 5 is a cross-sectional view of the channel structure 100 taken along the nano grating 130 along line D-D'. Referring to FIG. 5, the nano grating 130 is on the top surface of the first transparent substrate 101. The channel forming layer 103 is on the first transparent substrate 101 to entirely cover the nano grating 130. In addition, the junction layer 104 is on the channel forming layer 103. The plurality of nano channels 115 where portions of the junction layer 104 are absent and correspond to the nano channels 115 are positioned in a central portion of the junction layer 104, with the portions of the junction layer 104 between the nano channels 115 acting as barrier ribs. In one embodiment, the nano channels 115 may be formed by removing material portions of the junction layer 104. The second transparent substrate 102 is on the junction layer 104 to fully seal an upper portion of each of the nano channels 115. As illustrated in FIG. 5, the plurality of nano channels 115 may be positioned only in a region corresponding to the nano grating 130.

FIGS. 6A through 6F are cross-sectional views schematically illustrating an embodiment of a method of fabricating the above-described channel structure 100, taken along line B-B' of FIG. 1, according to the present invention. Hereinafter, the method of fabricating the channel structure 100 according to the present embodiment will be described with reference to FIGS. 6A through 6F.

Figure 6A:
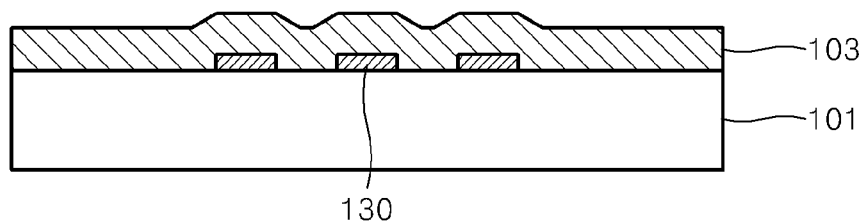
FIGS. 6A through 6F are cross-sectional views schematically illustrating an embodiment of a method of fabricating the channel structure of FIG. 1, taken along line B-B', according to the present invention.

First, referring to FIG. 6A, the nano grating 130 is formed directly on the first transparent substrate 101. In one embodiment, for example, an opaque nano grating material is stacked on all portions of the top surface of the first transparent substrate 101 to a predetermined thickness. The nano grating material is patterned by using lithography or the like such that the nano grating 130 having a pattern of a plurality of parallel bars arranged at regular intervals is formed. After that, the channel forming layer 103 may be formed directly on the first transparent substrate 101 to fully cover the nano grating 130. In one embodiment, for example, $SiO_2$ is deposited on the first transparent substrate 101 by using chemical vapor deposition ("CVD"), plasma-enhanced chemical vapor deposition ("PECVD"), physical vapor deposition ("PVD"), or the like, thereby forming the channel forming layer 103.

Figure 6B:
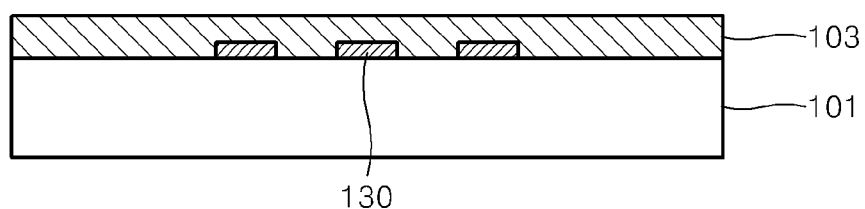

Due to the nano grating 130, the top surface of the channel forming layer 103 is uneven, as illustrated in FIG. 6A. Thus, after the channel forming layer 103 is formed, the top surface of the channel forming layer 103 is planarized by using a planarization technology such as chemical mechanical polishing ("CMP") until the top surface of the channel forming layer 103 is even, as illustrated in FIG. 6B.

Figure 6C:
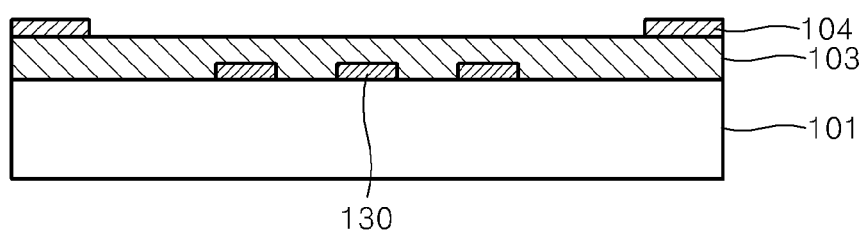

Subsequently, as illustrated in FIG. 6C, the junction layer 104 is formed directly on the channel forming layer 103. In one embodiment, for example, the junction layer 104 may include polysilicon and may be formed on all portions of the top surface of the channel forming layer 103 to a predetermined thickness. After that, portions of the junction layer 104 in regions in which the microchannels 110 and 120 and the nano channels 115 are to be formed may be removed using a patterning technology such as lithography and an etching technology. FIG. 6C illustrates a state where the portions of the junction layer 104 in the regions in which the microchannels 110 and 120 and the nano channels 115 are to be formed have been removed. In one embodiment, for example, the nano channels 115 may be formed by patterning portions of the junction layer 104 corresponding to the nano grating 130 in a direction perpendicular to the nano grating 130.

Figure 6D:
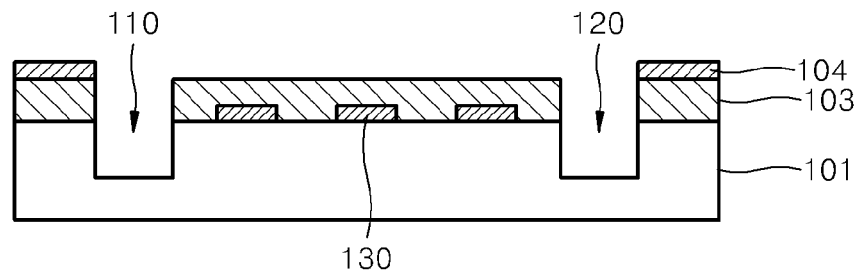

Next, as illustrated in FIG. 6D, the channel forming layer 103 and the first transparent substrate 101 are partially etched to form the pair of microchannels 110 and 120. In one embodiment, for example, after an etch mask is formed on the remaining region except for the region corresponding to the microchannels 110 and 120 by using a general etching technology, dry or wet etching may be performed. In one embodiment, for example, the pair of microchannels 110 and 120 may be formed to be physically and fluidly connected to end portions of the nano channels 115 as illustrated in FIG. 6C.

Figure 6E:
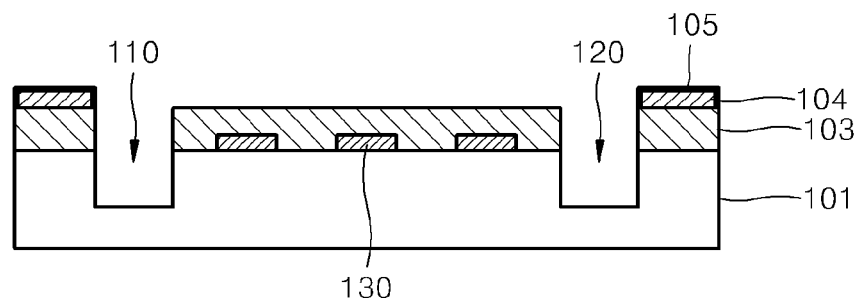

After the pair of microchannels 110 and 120 are formed, as illustrated in FIG. 6E, the junction layer 104 including polysilicon is heated to form the oxide layer 105 on exposed outer surfaces of the junction layer 104, as illustrated by the darker line in FIG. 6E. Since polysilicon has electrical conductivity, when an electrical field is applied to the channel structure 100 to move nano particles in a specimen in an electrophoresis method, a current may flow through the junction layer 104. The oxide layer 105 may insulate the surface of the junction layer 104 and may reduce or effectively prevent a current from flowing through the specimen or the like.

Figure 6F:
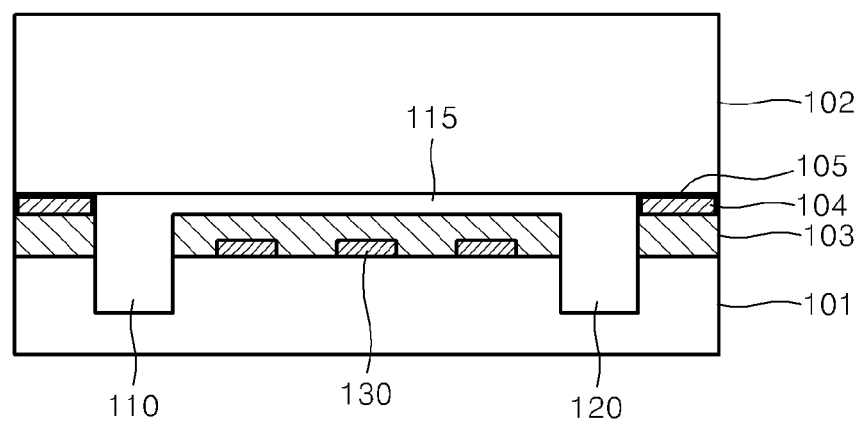

Lastly, as illustrated in FIG. 6F, the second transparent substrate 102 is bonded onto the junction layer 104. In one embodiment, for example, the second transparent substrate 102 may be bonded onto the junction layer 104 by using anodic bonding. Although not shown, after bonding is completed, the via holes 111, 112, 121, and 122 are formed through the second transparent substrate 102 and the junction layer 104 to be physically and fluidly connected to the end portions of the microchannels 110 and 120.

Figure 7:
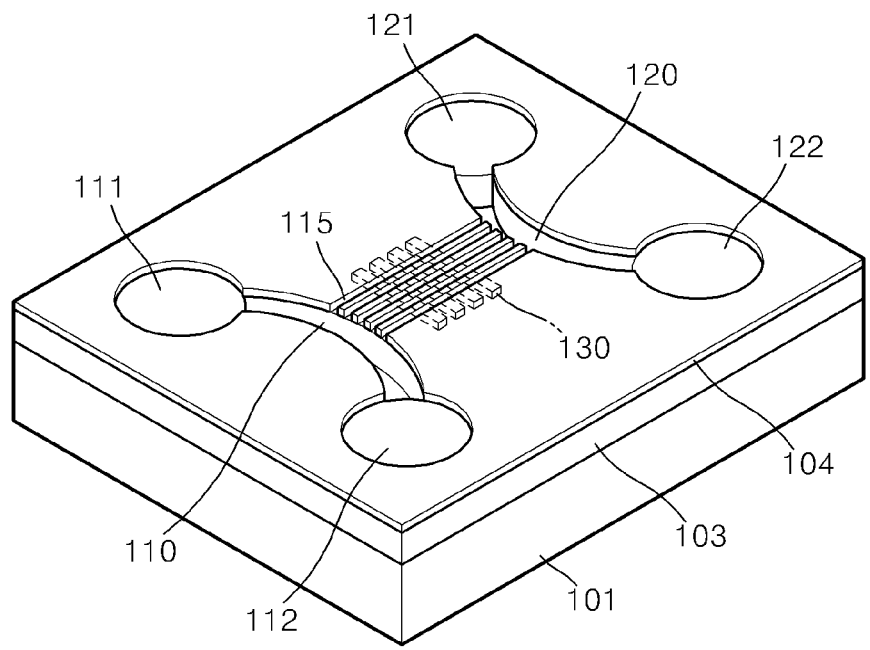
FIG. 7 is a perspective view schematically illustrating the channel structure of FIG. 1, without illustrating a second transparent substrate of the channel structure.

FIG. 7 is a perspective view schematically illustrating the channel structure 100 manufactured by the above-described method, without illustrating the second transparent substrate 102. Referring to FIG. 7, the channel forming layer 103 and the junction layer 104 are on the first transparent substrate 101. The microchannels 110 and 120 may be formed by partially removing the junction layer 104, the channel forming layer 103, and the first transparent substrate 101. In addition, bottom surfaces of the via holes 111, 112, 121, and 122 may be formed by removing portions of the junction layer 104 that contacts the end portions of the microchannels 110 and 120.

In FIG. 7, the bottom surfaces of the via holes 111, 112, 121, and 122 are formed by removing portions of only the junction layer 104 and are portions of the top surface of the channel forming layer 103. However, the channel forming layer 103 and the first transparent substrate 101 may be partially etched such that the via holes 111, 112, 121, and 122 and the microchannels 110 and 120 may have a common bottom surface in an alternative embodiment. In addition, as illustrated in FIG. 7, the nano channels 115 may be formed by patterning only the junction layer 104 between the microchannels 110 and 120, and at regular intervals between the microchannels 110 and 120. The nano grating 130 indicated by dotted lines may be below the nano channels 115 to cross the nano channels 115 perpendicularly.

Figure 8A:
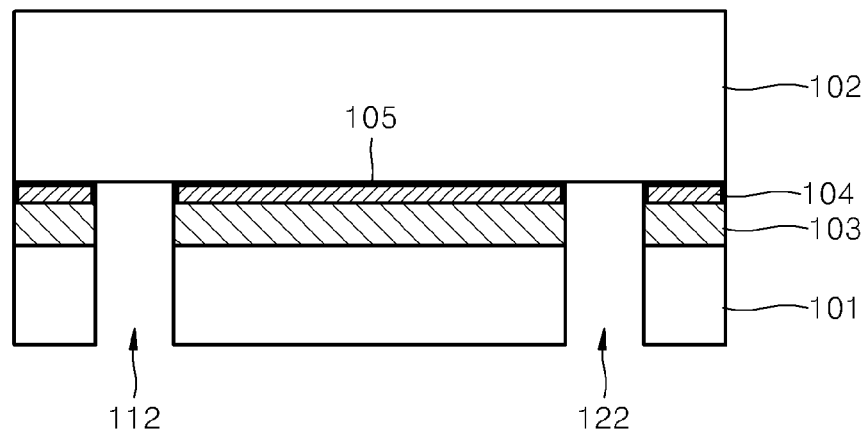
FIGS. 8A and 8B schematically illustrate another embodiment of a channel structure of a nano particle tracking device, according to the present invention.
Figure 8B:
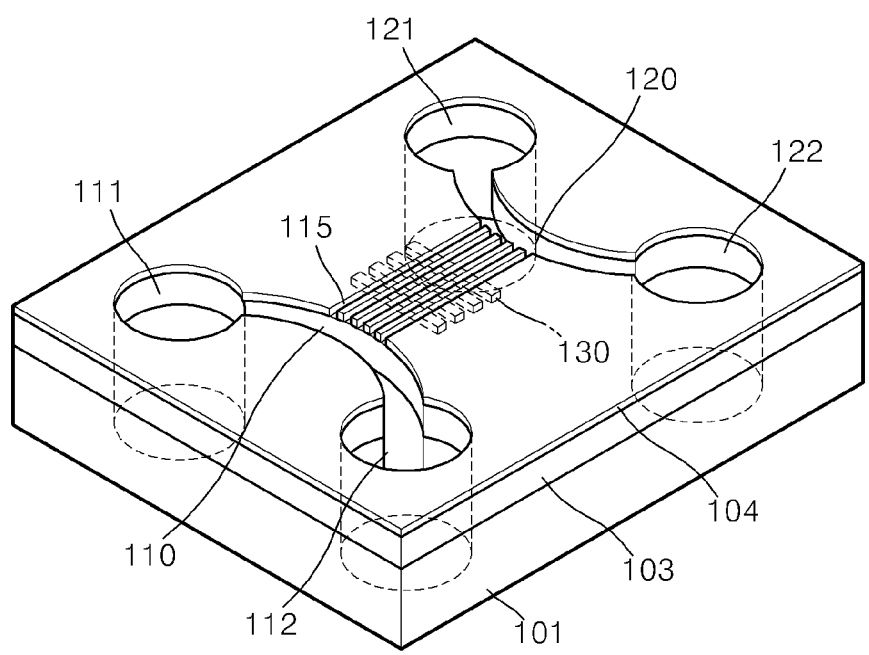

In an alternative embodiment, the via holes 111, 112, 121, and 122 may be extended completely through a thickness of the first transparent substrate 101 instead of the second transparent substrate 102. FIG. 8A illustrates a cross-sectional structure of another embodiment of the channel structure 100 according to the present invention along line C-C', in which via holes 112 and 122 extend completely through the first transparent substrate 101. Referring to FIG. 8A, the via holes 112 and 122 may extend through the first transparent substrate 101 to be physically and fluidly connected to the ends of the microchannels 110 and 120. In one embodiment, for example, the via holes 112 and 122 may extend through thicknesses of the first transparent substrate 101, the channel forming layer 103, and the junction layer 104, as illustrated in FIG. 8A, or only through the first transparent substrate 101. FIG. 8B is a perspective view illustrating an embodiment in which the via holes 111, 112, 121, and 122 extend through the first transparent substrate 101, the channel forming layer 103 and the junction layer 104. When the via holes 111, 112, 121, and 122 extend through the first transparent substrate 101, the second transparent substrate 102 may act only as a cover.

In the channel structure 100 described above, the second transparent substrate 102 is bonded onto the channel forming layer 103 via the junction layer 104, and the nano channels 115 are within the junction layer 104 only. However, without the junction layer 104, the nano channels 115 may be in the channel forming layer 103, and the second transparent substrate 102 may be bonded directly onto the channel forming layer 103.

FIGS. 9A through 9E are cross-sectional views schematically illustrating another embodiment of a method of fabricating a channel structure of a nano particle tracking device, according to the present invention. Hereinafter, the method of fabricating a channel structure of a nano particle tracking device, according to the present embodiment will be described with reference to FIGS. 9A through 9E.

Figure 9A:
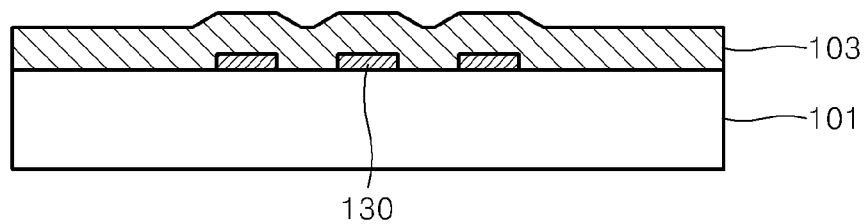
FIGS. 9A through 9E are cross-sectional views schematically illustrating another embodiment of a method of fabricating a channel structure of a nano particle tracking device, according to the present invention.
Figure 9B:
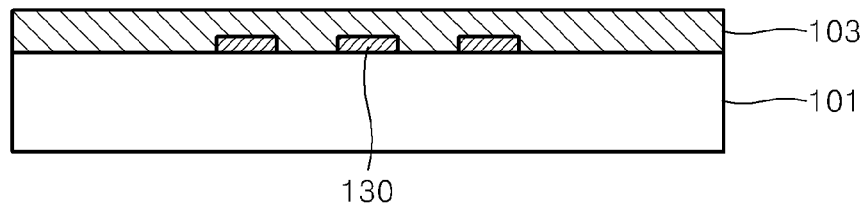

First, referring to FIG. 9A, the nano grating 130 is formed directly on the first transparent substrate 101. In one embodiment, for example, after an opaque nano grating material is deposited on all portions of the top surface of the first transparent substrate 101 to a predetermined thickness, the nano grating material is patterned by using lithography to form the nano grating 130. The channel forming layer 103 may be formed directly on the first transparent substrate 101 to fully cover the nano grating 130. In one embodiment, for example, the channel forming layer 103 may be formed by depositing $SiO_2$ on the first transparent substrate 101. After that, as illustrated in FIG. 9B, the top surface of the channel forming layer 103 is planarized such that the top surface of the channel forming layer 103 is even.

Figure 9C:
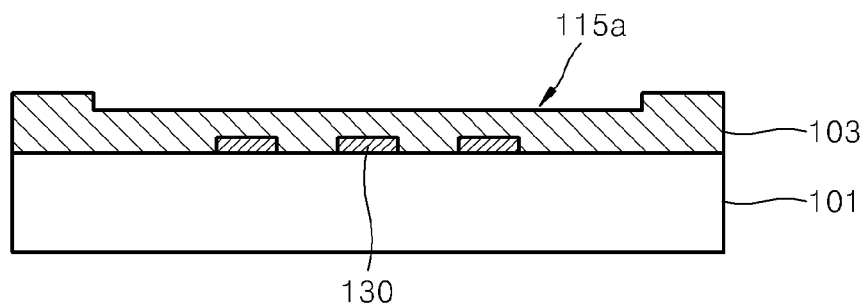

Subsequently, as illustrated in FIG. 9C, portions of the channel forming layer 103 corresponding to regions in which the microchannels 110 and 120 and nano channels 115 are to be formed may be removed by using a patterning technology such as lithography and an etching technology. In one embodiment, for example, in order to form the nano channels 115, the top surface of the channel forming layer 103 may be partially patterned in a direction perpendicular to the nano grating 130, as indicated by 115a in FIG. 9C. FIG. 9C illustrates a state where the channel forming layer 103 in the regions in which the microchannels 110 and 120 and the nano channels 115 are to be formed have been removed. A thickness of the channel forming layer 103 is smaller in the region 115a than in remaining regions.

Figure 9D:
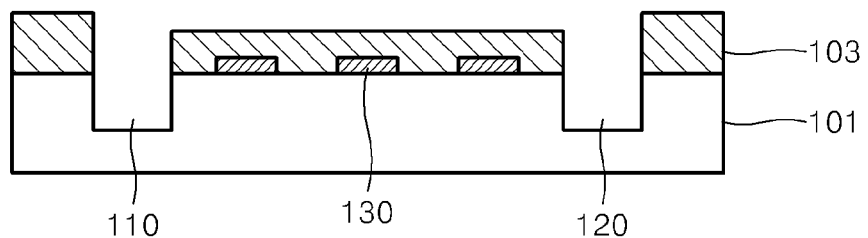

As illustrated in FIG. 9D, the channel forming layer 103 and the first transparent substrate 101 are partially etched to form the pair of microchannels 110 and 120 connected the end portions of the nano channels 115 formed in FIG. 9C. In one embodiment, for example, after an etch mask is formed on the remaining region except for the region corresponding to the microchannels 110 and 120 by using a general etching technology, dry or wet etching may be performed.

Figure 9E:
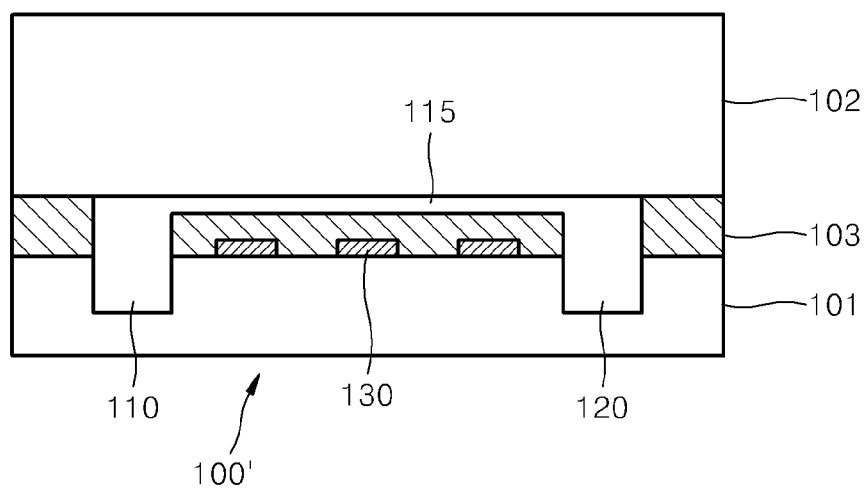

After the microchannels 110 and 120 are formed, as illustrated in FIG. 9E, the second transparent substrate 102 is bonded onto the channel forming layer 103. In one embodiment, for example, the second transparent substrate 102 may be bonded onto the channel forming layer 103 by using fusion bonding or an adhering method using an adhesive. Although not shown, the via holes 111, 112, 121, and 122 are formed through the second transparent substrate 102 to be connected to the end portions of the microchannels 110 and 120, thereby fabricating a channel structure 100' according to the present embodiment. In this regard, the top surface of the channel forming layer 103 may be partially etched to form the bottom surfaces of the via holes 111, 112, 121, and 122. That is, the thickness of the channel forming layer 103 at the bottom surface of the via holes 111, 112, 121, and 122, as well as at the region 115a (FIG. 9C) is smaller than remaining regions of the channel forming layer 103.

Figure 10:
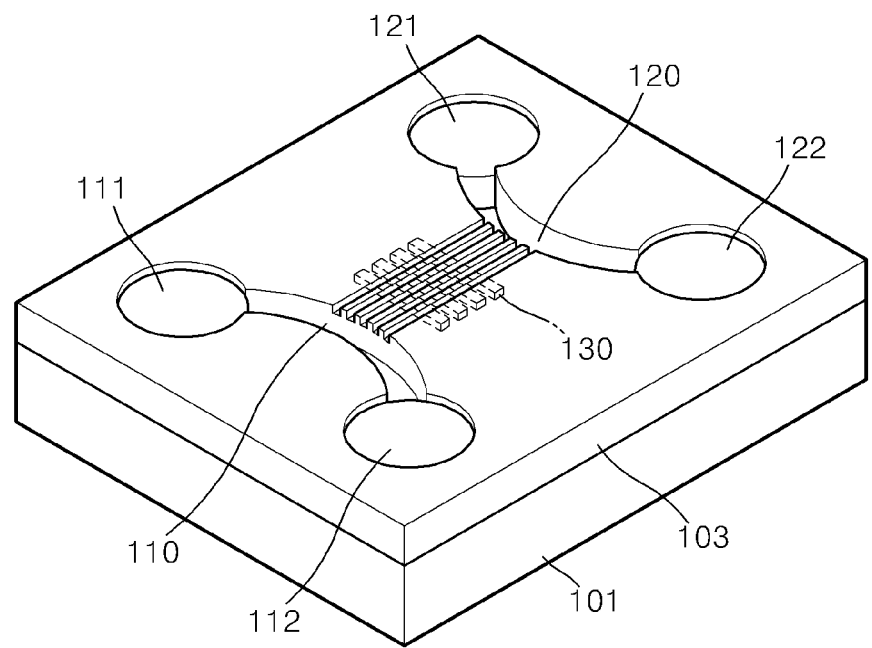
FIG. 10 is a perspective view schematically illustrating the channel structure fabricated by using the method of FIGS. 9A through 9E, without illustrating a second transparent substrate of the channel structure.

FIG. 10 is a perspective view schematically illustrating the channel structure 100' fabricated by using the method of FIGS. 9A through 9E, without illustrating the second transparent substrate 102. Referring to FIG. 10, the channel forming layer 103 is formed on the first transparent substrate 101. The microchannels 110 and 120 may also be formed by partially removing the channel forming layer 103 and the first transparent substrate 101. In addition, the bottom surfaces of the via holes 111, 112, 121, and 122 may be formed by etching portions of the channel forming layer 103 connected to the end portions of the microchannels 110 and 120.

In FIG. 10, the bottom surfaces of the via holes 111, 112, 121, and 122 are portions of the channel forming layer 103. However, the bottom surfaces of the via holes 111, 112, 121, and 122 may also be within the first transparent substrate 101, like the microchannels 110 and 120. In an alternative embodiment, for example, the via holes 111, 112, 121, and 122 and the microchannels 110 and 120 may have a common bottom surface. As illustrated in FIG. 8B, the via holes 111, 112, 121, and 122 may be extended completely through the thickness of the first transparent substrate 101 and the channel forming layer 103. In addition, as illustrated in FIG. 10, the nano channels 115 may be formed by partially patterning the top surface of the channel forming layer 103 between the microchannels 110 and 120. The nano grating 130 indicated by dotted lines in FIG. 10 may be on the top surface of the first transparent substrate 101 so as to cross the nano channels 115 below the nano channels 115, and may be covered by the channel forming layer 103.

Figure 11A:
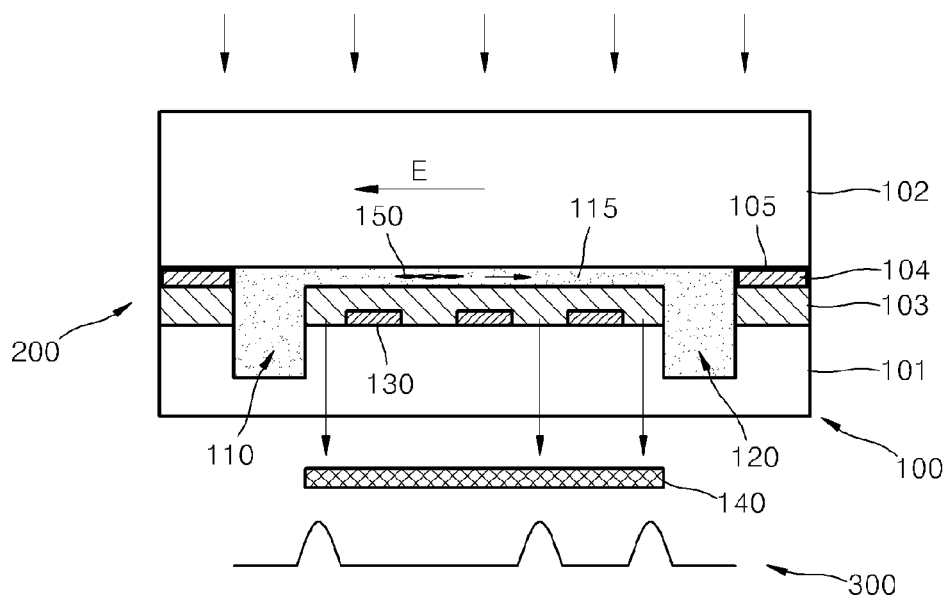
FIGS. 11A and 11B are cross-sectional views illustrating an embodiment of an operation of a nano particle tracking device according to the present invention.
Figure 11B:
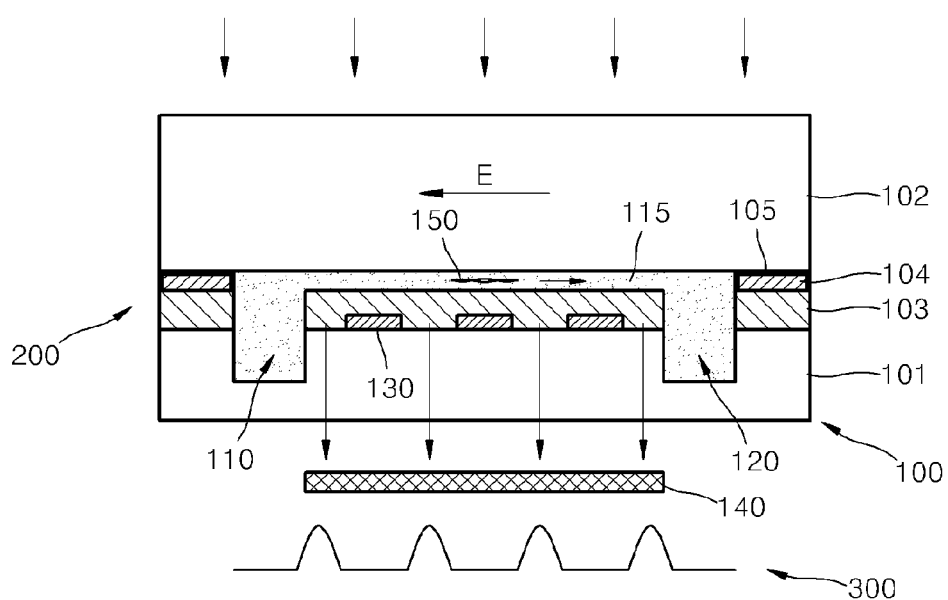

FIGS. 11A and 11B are cross-sectional views illustrating an embodiment of an operation of a nano particle tracking device 200 according to the present invention. Referring to FIG. 11A, the nano particle tracking device 200 according to the present embodiment may include the channel structure 100, and a photodetector 140 disposed below the channel structure 100. In the illustrated embodiment, for example, the photodetector 140 may be disposed below a region of the first transparent substrate 101 corresponding to (e.g., aligned or overlapping with) the nano channels 115. Although the channel structure 100 having the junction layer 104 fabricated by using the method of FIGS. 6A through 6F is illustrated in FIG. 11A, the channel structure 100' fabricated by using the method of FIGS. 9A through 9E may also be used. In addition, although FIG. 11A illustrates a case where the photodetector 140 is separated from the channel structure 100, the photodetector 140 may also be closely adhered to (e.g., contacting) a bottom surface of the channel structure 100. In this regard, the photodetector 140 may be a photomultiplier tube, a photodiode, or the like. One photodetector 140 may be disposed for each nano channel 115.

Hereinafter, an operation of measuring position information and movement speed of nano particles in a specimen by using the nano particle tracking device 200 according to the present embodiment will be described. First, referring to FIG. 11A, a specimen containing nano particles 150, for example, deoxyribonucleic acid ("DNA"), is inserted into and fills the microchannels 110 and 120. Then, nano particles 150 in the specimen are moved to the second microchannel 120 from the first microchannel 110 by using an electrophoresis method, for example. When DNA are to be moved between microchannels, an electrical field E in an opposite direction to a direction in which DNA are to be moved may be applied to the nano particle tracking device 200. The nano particles 150 which fill the first microchannel 110 are moved to the second microchannel 120 due to the electrical field E. In this case, the nano particles 150 pass through each of the nano channels 115 connected between the first microchannel 110 and the second microchannel 120. Since the width and the height of each nano channel 115 are nearly the same as sizes of the nano particles 150, the nano particles 150 may pass single-file through the nano channels 115.

While the nano particles 150 pass through the nano channels 115, light is irradiated onto the second transparent substrate 102, as illustrated by the downward arrows in FIG. 11A. Then, light may be transmitted to the photodetector 140 between the plurality of opaque bars of the nano grating 130 as illustrated by the further downward arrows in FIG. 11A. In order to prevent light from transmitting through the nano grating 130 to the photodetector 140, the nano grating 130 may be thicker in an irradiation direction of the light than a skin depth of the nano grating material in the same direction. In one embodiment, for example, when the nano grating 130 includes aluminum (Al), the thickness of the nano grating 130 may be greater than about 3.4 nm. When a width of each of the plurality of slits of the nano grating 130 (e.g., a distance between the opaque bars) is much less than a wavelength of visible light, for example, is less than about 100 nm, a near field generated due to a surface plasmon phenomenon (for example, an evanescent wave) may be detected by the photodetector 140.

A signal generated in the near field detected by the photodetector 140 is repeatedly changed when the nano particles 150 are moved over the nano grating 130. As illustrated in FIG. 11A, when the nano particles 150 are positioned on one of the plurality of slits, light is blocked thereat. On the other hand, as illustrated in FIG. 11B, when the nano particles 150 are positioned overlapping the opaque bars of the nano grating 130, light is not blocked thereat. Where light is not blocked, light is detected as illustrated by the protruding portions in wave line 300. Thus, when the nano particles 150 pass through the nano channels 115, a change in the intensity of light detected by the photodetector 140 is measured to determine position information and movement speed of the nano particles 150.

Figure 12A:
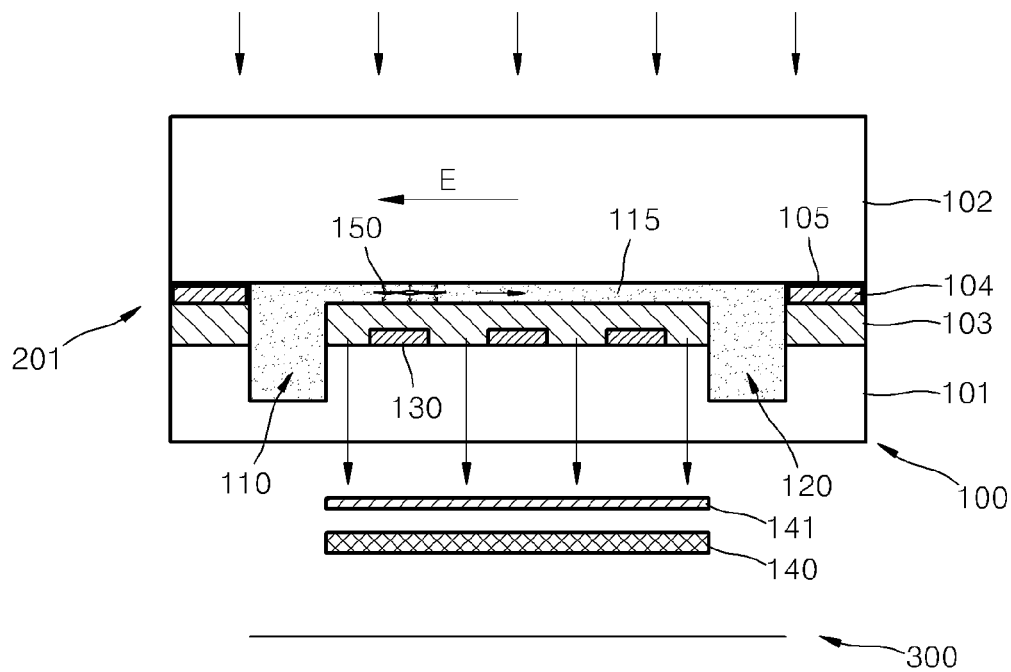
FIGS. 12A and 12B are cross-sectional views illustrating another embodiment of an operation of a nano particle tracking device according to the present invention.
Figure 12B:
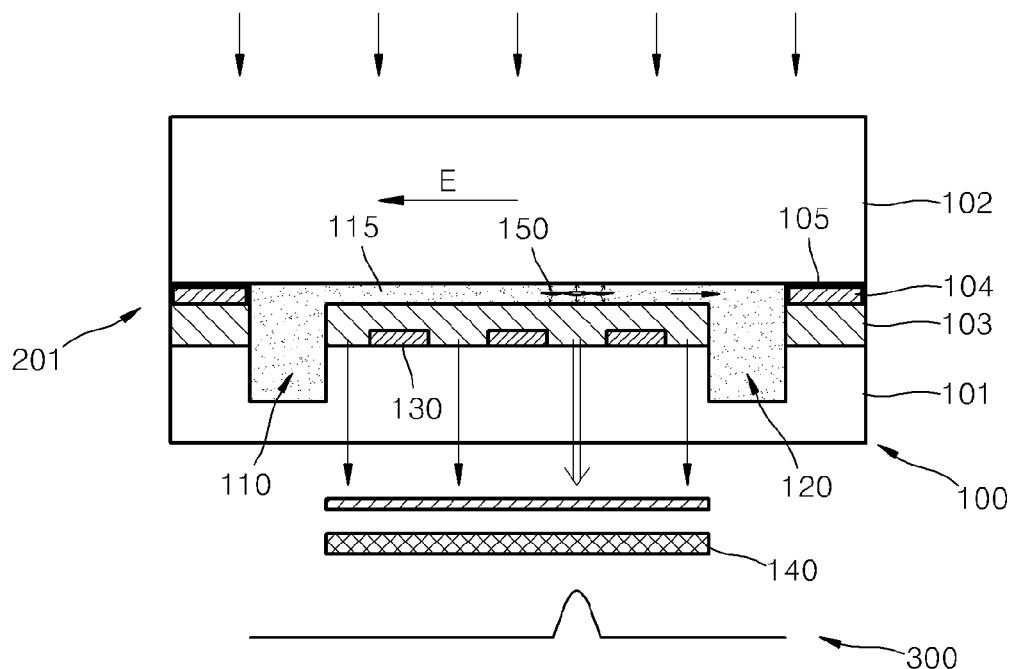

In FIGS. 11A and 11B, times at which light only externally generated is blocked by the nano particles 150 are measured. However, light may also be generated by the nano particles 150 in an alternative embodiment. FIGS. 12A and 12B are cross-sectional views illustrating another embodiment of an operation of a nano particle tracking device 201 according to the present invention. In FIGS. 12A and 12B, the nano particles 150 may be labeled with a phosphor material that is excited by externally generated light having a predetermined wavelength irradiated on the phosphor material. First, referring to FIG. 12A, the nano particle tracking device 201 may further include a band pass filter 141 disposed in front of the photodetector 140, i.e., between the photodetector 140 and the channel structure 100.

In the structure, the nano particles 150 are excited by a first light which is passed through the second transparent substrate 102, and emit a fluorescent second light. However, as illustrated in FIG. 12A, when the nano particles 150 are positioned on the opaque bars of the nano grating 130, the fluorescent light is blocked by the nano grating 130, and the photodetector 140 does not detect the fluorescent second light as illustrated by the flat wave line 300. On the other hand, as illustrated in FIG. 12B, when the nano particles 150 are positioned on the slits of the nano grating 130, the photodetector 140 may detect the fluorescent second light shown as a downward double-lined arrow emitted by the nano particles 150, as illustrated by the protruding portion in wave line 300. To this end, the band pass filter 141 may transmit only the fluorescent second light emitted by the nano particles 150 and may block other light such as the first light. Thus, when the nano particles 150 pass through the nano channel 115, a change in the intensity of the fluorescent second light detected by the photodetector 140 is measured to measure position information and movement speed of the nano particles 150.

As described above, according to an embodiment of the present invention, position information and movement speed of the nano particles 150 may be measured by using one single photodetector 140, such as a photodiode or photomultiplier tube. In one embodiment, for example, a change in the intensity of light measured by the photodetector 140 or on/off of the photodetector 140 is simply measured to measure position information and movement speed of the nano particles 150. Thus, the amount of data to be processed can be reduced compared to a method of analyzing a captured image by using a microscope and a charge coupled device ("CCD"). In addition, compared to a case where a CCD having limitations in response speed and signal processing speed is used, position information and movement speed of the nano particles 150 may be relatively quickly and precisely measured in real time.

While this invention has been particularly shown and described with reference to embodiments thereof, it will be understood by those skilled in the art that various changes in form and details may be made therein without departing from the spirit and scope of the invention as defined by the appended claims. The embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A channel structure of a nano particle tracking device, comprising:
    a pair of microchannels in which a specimen including nano particles is accommodated, and which face each other;
    at least one nano channel which is between the pair of microchannels, which connects the pair of microchannels to each other, and through which the nano particles in the specimen are moved between the pair of microchannels; and
    a nano grating below the nano channel and crossing the nano channel perpendicularly.

2. The channel structure of claim 1, wherein the nano grating comprises a pattern of a plurality of parallel opaque bars which are arranged at regular intervals.

3. The channel structure of claim 2, wherein a thickness of the nano grating is greater than a skin depth of a material of the nano grating.

4. The channel structure of claim 2, wherein a distance between adjacent parallel opaque bars is less than a wavelength of visible light.

5. The channel structure of claim 1, further comprising:
    a first transparent substrate;
    a channel forming layer on the first transparent substrate; and
    a second transparent substrate on the channel forming layer, the channel forming layer between the first and second transparent substrates.

6. The channel structure of claim 5, wherein
    the pair of microchannels extends through the channel forming layer and into the first transparent substrate,
    the nano channel is on an upper surface of the channel forming layer between the pair of microchannels, and
    the nano grating is on a top surface of the first transparent substrate between the pair of microchannels, and is covered by the channel forming layer.

7. The channel structure of claim 5, further comprising via holes through which the specimen is provided to the pair of microchannels, and connected to at least one of two end portions of each of the pair of microchannels.

8. The channel structure of claim 7, wherein the via holes extend completely through at least the first transparent substrate or completely through at least the second transparent substrate.

9. The channel structure of claim 1, further comprising:
    a first transparent substrate;
    a channel forming layer on the first transparent substrate;
    a junction layer on the channel forming layer, the channel forming layer between the first transparent substrate and the junction layer; and
    a second transparent substrate on the junction layer.

10. The channel structure of claim 9, wherein
    the pair of microchannels extends through the junction layer, the channel forming layer, and into the first transparent substrate,
    the nano channel is on an upper surface of the channel forming layer between the pair of microchannels, and
    the nano grating is on a top surface of the first transparent substrate between the pair of microchannels, and is covered by the channel forming layer.

11. The channel structure of claim 9, further comprising via holes through which the specimen is provided to the pair of microchannels, and connected to at least one of two end portions of each of the pair of microchannels.

12. The channel structure of claim 11, wherein the via holes extend completely through the second transparent substrate and the junction layer, or completely through at least the first transparent substrate.

13. The channel structure of claim 9, wherein the junction layer comprises polysilicon.

14. The channel structure of claim 13, wherein the junction layer includes an oxide layer which is an oxidized surface of the polysilicon.

15. A nano particle tracking device comprising:
    the channel structure of claim 1; and
    further comprising a photodetector opposite the nano channel with respect to the nano grating in a region overlapping the nano channel.

16. The nano particle tracking device of claim 15, further comprising a band pass filter between the channel structure and the photodetector.

17. The nano particle tracking device of claim 15, wherein
    the channel structure further comprises a plurality of nano channels, and
    further comprising one photodetector for each of the nano channels.

18. A method of fabricating a channel structure, the method comprising:
    forming a nano grating having a pattern of a plurality of parallel opaque bars arranged at regular intervals, on a top surface of a first transparent substrate;
    forming a channel forming layer on the first transparent substrate and covering the nano grating;
    forming a junction layer on the channel forming layer;
    forming nano channels in a direction perpendicular the nano grating by patterning portions of the junction layer corresponding to the nano grating;
    forming a pair of microchannels which is connected to end portions of each of the nano channels by partially etching the junction layer, the channel forming layer, and the first transparent substrate; and
    bonding a second transparent substrate directly onto the junction layer.

19. The method of claim 18, further comprising, after the channel forming layer is formed, planarizing a top surface of the channel forming layer.

20. The method of claim 18, wherein the junction layer comprises polysilicon.

21. The method of claim 20, further comprising, before the second transparent substrate is bonded onto the junction layer, forming an oxide layer covering the junction layer by oxidizing a surface of the junction layer.

22. The method of claim 18, wherein a thickness of the nano grating is greater than a skin depth of a material of the nano grating.

23. The method of claim 18, wherein a distance between adjacent parallel opaque bars is less than a wavelength of visible light.

24. The method of claim 18, further comprising forming via holes through the second transparent substrate and the junction layer, which are connected to an end portion of each of the microchannels.

25. The method of claim 18, further comprising forming via holes through the first transparent substrate, which are connected to an end portion of each of the microchannels.

26. A method of fabricating a channel structure, the method comprising:

forming a nano grating having a pattern of a plurality of parallel opaque bars arranged at regular intervals on a top surface of a first transparent substrate;

forming a channel forming layer on the first transparent substrate and covering the nano grating;

forming nano channel in a direction perpendicular to the nano grating by patterning portion of a top surface of the channel forming layer corresponding to the nano grating, such that a thickness of the channel forming layer corresponding to the nano channel is smaller than remaining portions of the channel forming layer;

forming a pair of microchannels which is connected to end portions the nano channel by partially etching the channel forming layer and the first transparent substrate; and bonding a second transparent substrate directly onto the channel forming layer.

27. The method of claim 26, further comprising, forming via holes through at least the first transparent substrate or through at least the second transparent substrate, the via holes connected to an end portion of each of the microchannels.

* * * * *